United States Patent [19] [11] 4,232,174
Statz et al. [45] Nov. 4, 1980

[54] CATALYST AND DEHYDROGENATION PROCESS

[75] Inventors: Robert J. Statz; James K. Doty, both of Wilmington, Del.

[73] Assignee: E. I. Du Pont de Nemours and Company, Wilmington, Del.

[21] Appl. No.: 24,858

[22] Filed: Mar. 28, 1979

[51] Int. Cl.$^2$ .................. C07C 57/02; C07C 69/52
[52] U.S. Cl. ............................. 562/599; 560/214; 252/435; 252/437
[58] Field of Search ............ 560/214; 562/599; 252/435, 437

[56] References Cited

U.S. PATENT DOCUMENTS

| | | | |
|---|---|---|---|
| 3,855,279 | 12/1974 | Watkins | 560/214 |
| 3,862,910 | 1/1975 | Achowski | 252/435 |
| 3,948,959 | 4/1976 | Cavalerra et al. | 562/599 |
| 4,029,695 | 6/1977 | Watkins | 560/214 |

*Primary Examiner*—Winston A. Douglas
*Assistant Examiner*—J. V. Howard

[57] ABSTRACT

A catalyst containing alkali metal, chromium, iron, lead, phosphorus and oxygen, and a process for the preparation of unsaturated lower aliphatic acids and esters of such acids by catalytic oxidative dehydrogenation of the corresponding saturated acids and esters using the catalyst.

4 Claims, No Drawings

CATALYST AND DEHYDROGENATION PROCESS

BACKGROUND OF THE INVENTION

Unsaturated lower aliphatic acids and esters, and particularly methacrylic acid and its esters, are used in the preparation of polymers which find wide commercial applicability.

The preparation of such unsaturated lower aliphatic acids and esters is typically carried out by the catalytic oxidative dehydrogenation of the corresponding saturated acids and esters. A wide variety of catalysts has been proposed for such reactions. However, the catalysts previously proposed share one or more deficiencies. Earlier catalysts, for example, frequently result in an undesirably low conversion in the catalytic process or low selectivity for the desired unsaturated acid product. Others exhibit short catalytic life or higher cost than would be commercially acceptable. Accordingly, continued effort has been directed toward the development of better catalysts for this oxidative dehydrogenation reaction.

SUMMARY OF THE INVENTION

The present invention provides an improved catalyst that results in high selectivity and yield in the oxidative dehydrogenation of saturated lower aliphatic acids and esters to the corresponding unsaturated acids and esters.

Specifically, the instant invention provides a catalyst of the general formula:

$$Me_aCr_bFePb_cP_dO_e$$

wherein Me is an alkali metal, a is about from 0.01 to 0.3, b is about from 0.05 to 0.4, c is about from 0.6 to 1.0, d is about from 1.0 to 6.0 and e is sufficient to provide oxygen to satisfy the oxidative states of the remaining components.

The instant invention further provides an improvement in the process for the oxidative dehydrogenation of lower aliphatic saturated acids and esters of such acids by heating in the presence of a catalyst to yield the corresponding unsaturated lower aliphatic acids and esters, which improvement comprises using a catalyst of the above formula.

DESCRIPTION OF THE INVENTION

The present invention is based on the discovery of a phosphate catalyst containing alkali metal, chromium, iron, and lead as shown by the above formula which is particularly well suited for the dehydrogenation reaction used to produce unsaturated acids and esters such as methacrylic acid.

The catalyst of the present invention can be readily prepared by first dissolving salts of the required metals in water to form a solution. While any water-soluble salt of the metal can be used, such as nitrates and chlorides, nitrates of the required metals have been found to be particularly satisfactory. For example, the iron component of the catalyst can be provided from ferric nitrate enneahydrate; chromium can be provided from chromium nitrate enneahydrate; lead can be provided from lead nitrate and the alkali metal from its corresponding nitrate.

The phosphorus in the catalytic compound can be conveniently provided by adding, to the metal salt solution, an amount of phosphoric acid or dibasic ammonium hydrogen phosphate necessary to provide the desired amount of phosphorus in the final product.

After preparation of an aqueous solution containing the alkali metal, chromium, iron, lead, and phosphorus components of the catalyst, the solution can be precipitated by the addition of concentrated ammonium hydroxide to form a more basic solution, having a pH, for example, of about 5.0. The resulting precipitated catalytic components can then be filtered, washed and calcined with oxygen to complete the reaction to the desired catalytic compound. Typically, the composition is calcined at about 500° C. for two hours or more.

The alkali metal used in the preparation of the catalysts can be selected from one or more of lithium, sodium, potassium, rubidium and cesium. However, of these, sodium, potassium and cesium are preferred for their contribution to high selectivity, and sodium and cesium are particularly preferred.

The present catalysts can be used in conjunction with various supports conventionally used for catalysts of this type, including pumice, Kieselguhr, zirconium dioxide and colloidal silica. However, collodial silica has been found to be particularly satisfactory in the present invention, providing increased conversion. While this effect is not fully understood, it is believed to be a function of the increased surface area provided by the silica support. The colloidal silica can be conveniently incorporated into the catalyst by adding the colloidal silica to the solution of catalyst components before precipitation and calcination.

The catalytic dehydrogenation for which the catalysts are particularly well suited involves contacting saturated lower aliphatic acids and esters with oxygen in the presence of the catalyst at elevated temperatures. Conventional fixed tube or fluid bed reactors can be used for this conversion. The general conversion process is well known in the art and described, for example, in U.S. Pat. No. 3,652,654. The acids or esters used in the reaction have the general formula $$R_1-CH-CH-\overset{O}{\overset{\|}{C}}-O\,R_4 \atop R_2 \;\; R_3$$

wherein each of $R_1$, $R_2$, $R_3$ and $R_4$ is selected from hydrogen and lower alkyl groups containing 1-4 carbon atoms. In the instant process, the conversion temperatures used are generally about from 250° to 500° C., and preferably about from 325° to 400° C. The pressure, for ease of operation, is generally maintained at atmospheric pressure or somewhat above. However, pressures within the range of 1-10 atmospheres can be used effectively.

The instant process is particularly well suited to the conversion of isobutyric acid to methacrylic acid. The use of the present catalysts in this process results in good conversions with excellent selectivity for the desired methacrylic acid as opposed to acetone or other by-products.

The instant invention is further illustrated by the following specific examples, in which parts and percentages are by weight unless otherwise indicated.

EXAMPLES

In Examples 1–14 and Comparative Examples A–H, the catalytic compositions were prepared by first forming a solution of ferric nitrate enneahydrate, chromium nitrate enneahydrate, alkali metal nitrate and lead nitrate in distilled water at 50° C., each of the nitrates being present in quantities that will result in the desired atomic ratio of the metal in the final product. To this solution was added 85% phosphoric acid, also in quantities sufficient to provide the required amount of phosphorus in the final product. This solution was stirred for ten minutes, and had a highly acidic character, exhibiting a pH of less than 1.0.

In those examples using colloidal silica as a catalyst support, the silica was added to the solution with additional stirring for ten minutes.

The catalytic components were precipitated from solution by the addition of ammonium hydroxide in an amount sufficient to adjust the pH of the solution to 5.0. After precipitation, the slurry was heated at 100° C. for two to three hours to assure precipitation of the silica, when present. The slurry was then cooled to room temperature, filtered, and washed three times with water. The resulting catalyst cake was dried in a vacuum oven at 140° C. for eight hours, broken into four to ten mesh particles, and calcined at 500° C. for two hours with oxygen.

The resulting catalyst was broken into particles of 8 to 10 mesh for fixed bed reactors, and 100 to 170 mesh for fluidized bed reactors.

In Examples 1–8 and Comparative Examples A–C, a fixed bed catalytic process was used for the conversion of isobutyric acid to methacrylic acid. The catalyst granules, prepared as described above, were packed in a ⅜ in. stainless steel fixed bed reactor. About 1.2 cc of catalyst having an 8 to 10 mesh particle size were used. The liquid isobutyric acid was continuously vaporized and mixed with air and the mixed gases were preheated and fed to the reactor. The temperature was maintained by heating the reactor with a fluidized sand bath. The contact times are expressed as the ratio of catalyst volume to total gas feed rate, and calculated assuming ideal gas behavior. The units used are cubic centimeters of catalyst per cubic centimeters of gas feed per second at 25° C. and 760 millimeters of mercury.

In Examples 1–8 and Comparative Examples A–C, conversion and selectivity are determined based upon the total moles of isobutyric acid in the feed stream and the total moles of isobutyric acid and methacrylic acid contained in product stream. Percent conversion is calculated by subtracting the moles of isobutyric acid recovered from the moles of isobutyric acid introduced into the reactor, dividing by the moles of isobutyric acid introduced, and multiplying by 100. The percent selectivity is the moles of product formed divided by the difference in the moles of isobutyric acid introduced into the system and the moles of isobutyric acid recovered, multiplied by 100. The quantities of product used in these calculations is determined by gas chromographic analysis of the product stream taken from the reactor.

In Examples 7 and 8, large pore silica catalyst supports with low surface areas were used in place of the colloidal silica. Pumice was used in Example 7 and Kieselguhr was used in Example 8. The catalyst were prepared as previously described, except that pumice or Kieselguhr was added to the aqueous solution instead of the colloidal silica.

The catalytic compounds used in Comparative Examples A–C were prepared according to German Patent Publication No. 2438646.

In Examples 9–16, the catalysts of indicated composition were ground and screened through a 100 mesh screen and retained on a 170 mesh screen. These catalysts were used in a fluidized bed reactor which consisted of a 1 inch outer diameter stainless steel tube fitted with a 30 micron sintered metal disk on the bottom. A mixture of air, water and isobutyric acid in the indicated ratios was fed continuously to the bottom of the reactor, the temperature which was controled by means of a fluidized sand bath.

The atomic ratios of the catalysts used, the operating conditions and the results of the Examples are summarized in the following Tables I to III.

TABLE I

OXIDATIVE DEHYDROGENATION OF ISOBUTYRIC ACID FLUIDIZED BED PROCESS

| | Catalyst Composition (Atomic Ratio) | | | | | | |
|---|---|---|---|---|---|---|---|
| | Me | | | | | | Silica |
| Example | Metal | Ratio | Fe | Pb | Cr | P | Support |
| 1 | Cs | 0.1 | 1.0 | 0.9 | 0.25 | 4.7 | — |
| 2 | Cs | 0.1 | 1.0 | 0.9 | 0.25 | 4.7 | 3.0 |
| 3 | Na | 0.01 | 1.0 | 0.8 | 0.11 | 4.2 | — |
| 4 | Cs | 0.07 | 1.0 | 0.8 | 0.11 | 4.4 | 2.65 |
| 5 | K | 0.07 | 1.0 | 0.8 | 0.11 | 4.4 | 2.65 |
| 6 | Na | 0.07 | 1.0 | 0.8 | 0.11 | 4.4 | 2.65 |
| 7 | Na | 0.07 | 1.0 | 0.8 | 0.11 | 4.4 | — |
| 8 | Na | 0.07 | 1.0 | 0.8 | 0.11 | 4.4 | — |
| 9 | Cs | 0.1 | 1.0 | 0.9 | 0.25 | 4.7 | — |
| 10 | Cs | 0.1 | 1.0 | 0.9 | 0.25 | 4.7 | 3.0 |
| 11 | Cs | 0.07 | 1.0 | 0.8 | 0.11 | 4.4 | 2.65 |
| 12 | K | 0.07 | 1.0 | 0.8 | 0.11 | 4.4 | 2.65 |
| 13 | Na | 0.07 | 1.0 | 0.8 | 0.11 | 4.4 | 2.65 |
| 14 | Na | 0.07 | 1.0 | 0.8 | 0.11 | 4.4 | 2.65 |
| A | — | — | 1.0 | 0.6 | — | 3.3 | — |
| B | — | — | 1.0 | 0.6 | — | 3.3 | — |
| C | — | — | 1.0 | 0.6 | — | 3.3 | 1.6 |
| D | Bi 2.0 | Bi 2.0 | 1.0 | — | — | 3.0 | — |
| E | Bi 2.0 | Bi 2.0 | 1.0 | — | — | 3.0 | — |
| F | Cs | 0.66 | 1.0 | — | — | 1.84 | — |
| G | — | — | 1.0 | 0.6 | — | 3.3 | 1.6 |
| H | Cs | 0.66 | 1.0 | — | — | 1.84 | — |

TABLE II

| | Reaction Conditions | | | | |
|---|---|---|---|---|---|
| Example | Temp ° C. | Mole % IBA | Mole % AIR | Mole % H₂O | Contact Time Sec |
| 1 | 400° | 13.5 | 32.5 | 54.0 | 0.22 |
| 2 | 400° | 13.5 | 32.5 | 54.0 | 0.22 |
| 3 | 400° | 13.5 | 32.5 | 54.0 | 0.30 |
| 4 | 400° | 8.0 | 18.5 | 73.5 | 0.28 |
| 5 | 400° | 8.0 | 18.5 | 73.5 | 0.30 |
| 6 | 400° | 8.0 | 18.5 | 73.5 | 0.26 |
| 7 | 400° | 8.0 | 18.5 | 73.5 | 0.26 |
| 8 | 400° | 8.0 | 18.5 | 73.5 | 0.26 |
| 9 | 400° | 15 | 22.6 | 61.9 | 1.43 |
| 10 | 399° | 7.4 | 21.1 | 71.2 | 1.01 |
| 11 | 350° | 8.1 | 18.6 | 73.3 | 2.33 |
| 12 | 376° | 7.9 | 70.3 | 71.8 | 1.71 |
| 13 | 350° | 8.04 | 19.2 | 73.1 | 2.90 |
| 14 | 350° | 7.9 | 20.7 | 71.4 | 2.49 |
| A | 400° | 13.5 | 32.5 | 54.0 | 0.22 |
| B | 400° | 8.0 | 18.5 | 73.5 | 0.26 |
| C | 400° | 8.0 | 18.5 | 73.5 | 0.30 |
| D | 400° | 13.5 | 32.5 | 54.0 | 0.22 |
| E | 400° | 8.0 | 18.5 | 73.5 | 0.28 |
| F | 400° | 8.0 | 18.5 | 73.5 | 0.28 |
| G | 389° | 15.5 | 23.0 | 62.0 | 1.70 |
| H | 350° | 8.0 | 21.0 | 70.9 | 2.35 |

TABLE III

| Example | % Conversion | % Selectivity MAA | % Selectivity Acetone |
|---|---|---|---|
| 1 | 30.6 | 83.9 | 15.7 |
| 2 | 22.0 | 84.8 | 14.5 |
| 3 | 34.8 | 80.0 | 13.0 |
| 4 | 51.8 | 80.8 | 12.4 |
| 5 | 57.8 | 83.4 | 13.8 |
| 6 | 55.0 | 84.5 | 11.8 |
| 7 | 6.9 | 81.6 | 19.1 |
| 8 | 30.0 | 82.0 | 14.6 |
| 9 | 57.5 | 66.0 | 15.2 |
| 10 | 49.5 | 79.4 | 10.3 |
| 11 | 35.0 | 78.1 | 16.6 |
| 12 | 53.1 | 77.6 | 15.4 |
| 13 | 62.8 | 85.0 | 13.0 |
| 14 | 39.5 | 85.5 | 10.4 |
| A | 29.0 | 70.0 | 14.6 |
| B | 33.3 | 63.1 | 12.5 |
| C | 36.7 | 51.7 | 13.5 |
| D | 34.8 | 71.9 | 28.2 |
| E | 33.5 | 70.3 | 27.1 |
| F | 36.8 | 44.6 | 13.8 |
| G | 58.2 | 64.0 | 10.6 |
| H | 39.4 | 62.2 | 12.5 |

We claim:

1. In the process for the oxidative dehydrogenation of a saturated compound of the general formula:

$$R_1-\underset{R_2}{CH}-\underset{R_3}{CH}-\overset{O}{\underset{\|}{C}}-OR_4$$

wherein each of $R_1$, $R_2$, $R_3$ and $R_4$ is selected from hydrogen and lower alkyl groups containing 1–4 carbon atoms, by heating the compound in the presence of a catalyst and oxygen to yield the corresponding unsaturated compound, the improvement which comprises heating the compound in the presence of a catalyst of the general formula:

$$Me_aCr_bFePb_cP_dO_e$$

wherein Me is an alkali metal selected from the group consisting of lithium, sodium, potassium, rubidium, and cesium, a is about from 0.01 to 0.3, b is about from 0.05 to 0.4, c is about from 0.6 to 1.0, d is about from 1.0 to 6.0 and e is sufficient to provide oxygen to satisfy the oxidative states of the remaining components.

2. A process of claim 1 wherein the alkali metal of the catalyst is potassium, sodium or cesium.

3. A process of claim 1 wherein the catalyst further comprises a support of colloidal silica.

4. A process of claim 1 wherein the saturated compound is isobutyric acid.

* * * * *